(12) United States Patent
Peng et al.

(10) Patent No.: US 8,309,918 B2
(45) Date of Patent: Nov. 13, 2012

(54) TRACE DETECTOR AND ANALYTICAL METHOD FOR TRACE DETECTOR

(75) Inventors: Hua Peng, Beijing (CN); Jin Lin, Beijing (CN); Wen He, Beijing (CN); Yangtian Zhang, Beijing (CN); Yaoxin Wang, Beijing (CN); Peng Jiao, Beijing (CN); Hui Li, Beijing (CN); Zhongxia Zhang, Beijing (CN)

(73) Assignee: Nuctech Company Limited, Beijing (CN)

( * ) Notice: Subject to any disclaimer, the term of this patent is extended or adjusted under 35 U.S.C. 154(b) by 252 days.

(21) Appl. No.: 12/747,243

(22) PCT Filed: Dec. 30, 2009

(86) PCT No.: PCT/CN2009/076280
§ 371 (c)(1),
(2), (4) Date: Jun. 10, 2010

(87) PCT Pub. No.: WO2010/135899
PCT Pub. Date: Dec. 2, 2010

(65) Prior Publication Data
US 2011/0139975 A1 Jun. 16, 2011

(30) Foreign Application Priority Data
May 25, 2009 (CN) .......................... 2009 1 0085555

(51) Int. Cl.
*H01J 49/04* (2006.01)

(52) U.S. Cl. ...... 250/288; 250/286; 250/287; 73/863.23

(58) Field of Classification Search .................. 250/288, 250/286, 287; 73/863.23, 863.33, 864
See application file for complete search history.

(56) References Cited

U.S. PATENT DOCUMENTS
5,491,337 A * 2/1996 Jenkins et al. ................ 250/287
(Continued)

FOREIGN PATENT DOCUMENTS
WO   WO2006129101   12/2006
(Continued)

OTHER PUBLICATIONS
First Chinese Office Action (without English translation) for corresponding Chinese Application No. 200910085555.X, dated Feb. 16, 2012, 4 pages.
(Continued)

*Primary Examiner* — Kiet T Nguyen
(74) *Attorney, Agent, or Firm* — Westman, Champlin & Kelly, P.A.

(57) ABSTRACT

A trace detector is disclosed. The trace detector comprises: a desorption chamber defining a desorption region, and the desorption chamber has a housing. The housing has a sample feeding port for introducing a substance to be detected into the desorption chamber and a gas discharge port for discharging gas entraining the sample from the desorption chamber. A controller is used for controlling the trace detector in such a manner that the sample feeding port and the gas discharge port are in fluid communication with the desorption chamber during pre-concentration process of the trace detector, thereby continuously feeding and collecting the sample. With the above manner, data collecting, processing and analyzing processes may be performed by the trace detector throughout the sample feeding process and the gas pre-concentrating process. The trace detector has an excellent detecting period of time whether the substance to be detected in the gas is in a high concentration state or a low concentration state, and the trace detector can perform continuous sampling for a long time, thereby improving a ratio of the amount of trapped substance to the amount of the substance entrained in the gas to be detected and the amount of the cumulated trapped substance, decreasing the probability of failing to detect the substance, and increasing detection sensitivity. In addition, the detection efficiency of the detector is increased during the gas pre-concentration process.

10 Claims, 1 Drawing Sheet

U.S. PATENT DOCUMENTS

| | | | | |
|---|---|---|---|---|
| 5,854,431 | A * | 12/1998 | Linker et al. | 73/863.23 |
| 6,765,198 | B2 | 7/2004 | Jenkins et al. | 250/287 |
| 7,275,453 | B2 * | 10/2007 | Ishikawa et al. | 73/864.33 |
| 7,399,958 | B2 | 7/2008 | Miller et al. | 250/286 |
| 7,511,268 | B2 | 3/2009 | Landgraf | 250/288 |
| 2008/0206106 | A1 | 8/2008 | Fernandez de la Mora | 422/83 |
| 2009/0090196 | A1 | 4/2009 | Clark et al. | 73/863.12 |

FOREIGN PATENT DOCUMENTS

| | | |
|---|---|---|
| WO | WO2007113486 | 10/2007 |
| WO | WO 2008/074981 | 6/2008 |

OTHER PUBLICATIONS

Search Report from PCT/CN2009/076280, dated Feb. 10, 2010.
Written Opinion from PCT/CN2009/076280, dated Apr. 1, 2010.
First Office Action issued by the Canadian Intellectual Property Office for Canadian Application No. 2,705,956, dated Nov. 3, 2010.
Supplementary European Search Report for corresponding European Application No. 09845115.6, dated Aug. 7, 2012, 3 pages.
Office Action for corresponding European Application No. 09845115.6, dated Aug. 20, 2012, 4 pages.

* cited by examiner

TRACE DETECTOR AND ANALYTICAL METHOD FOR TRACE DETECTOR

CROSS-REFERENCE TO RELATED APPLICATION

This Application is a Section 371 National Stage Application of International Application No. PCT/CN2009/076280, filed Dec. 30, 2009, the contents of which are hereby incorporated by reference in their entirety.

BACKGROUND OF THE INVENTION

1. Field of the Invention

The present invention relates to a trace detector and an analytical method for a trace detector, and particularly to a trace detector, such as an ion mobility spectrometer, for detecting explosives, narcotics and the like, which is capable of continuously feeding sample by means of gas and pre-concentrating the gas entraining the sample, and an analytical method for a trace detector which is capable of continuously feeding sample by means of gas and pre-concentrating the gas entraining the sample.

2. Description of the Related Art

Conventionally, there are two sample feeding methods using gas which are used for an ion mobility spectrometer for detecting explosives, narcotics and the like: one is an analytical method in which sample is continuously fed and collected without pre-concentration process of the gas, and the other one is an analytical method in which the gas is pre-concentrated, but the pre-concentration process and a sample feeding process are independent of each other.

SUMMARY OF THE INVENTION

It is therefore an object of the present invention to provide a trace detector and an analytical method for a trace detector which are capable of not interrupting gas detecting or analyzing course while performing gas pre-concentrating process to improve a ratio of the amount of trapped substance to the amount of the substance entrained in the gas to be detected and the amount of the cumulated trapped substance, to decrease the probability of failing to detect the substance, and to increase detection sensitivity.

According to an aspect of the present invention, there is provided a trace detector. The trace detector comprises a desorption chamber defining a desorption region. The desorption chamber has a housing. The housing has a sample feeding port for introducing a substance to be detected into the desorption chamber and a gas discharge port for discharging gas entraining the sample from the desorption chamber. The trace detector further comprises a controller for controlling the trace detector in such a manner that the sample feeding port and the gas discharge port are in fluid communication with the desorption chamber during pre-concentration process of the trace detector, thereby continuously feeding and collecting the sample.

According to another aspect of the present invention, there is provided an analytical method for a trace detector. The method comprises the steps of: continuously feeding sample into a desorption chamber of the trace detector; continuously discharging gas entraining the sample from the desorption chamber; and pre-concentrating the gas entraining the sample or the sample gas in the desorption chamber while continuously feeding sample into the desorption chamber and continuously discharging the gas entraining the sample.

With the above manners, the sample feeding process by gas is not interrupted while performing the gas pre-concentrating process, thereby improving a ratio of the amount of trapped substance to the amount of the substance entrained in the gas to be detected and the amount of the cumulated trapped substance, decreasing the probability of failing to detect the substance, and increasing detection sensitivity. In addition, data collecting, processing and analyzing processes may be performed by the trace detector throughout the sample feeding process and the gas pre-concentrating process. The trace detector has an excellent detecting period of time regardless of the substance to be detected in the gas being in a high concentration state or a low concentration state, and the trace detector can perform continuous sampling for a long time.

DETAILED DESCRIPTION OF THE EMBODIMENTS

Figure 1:
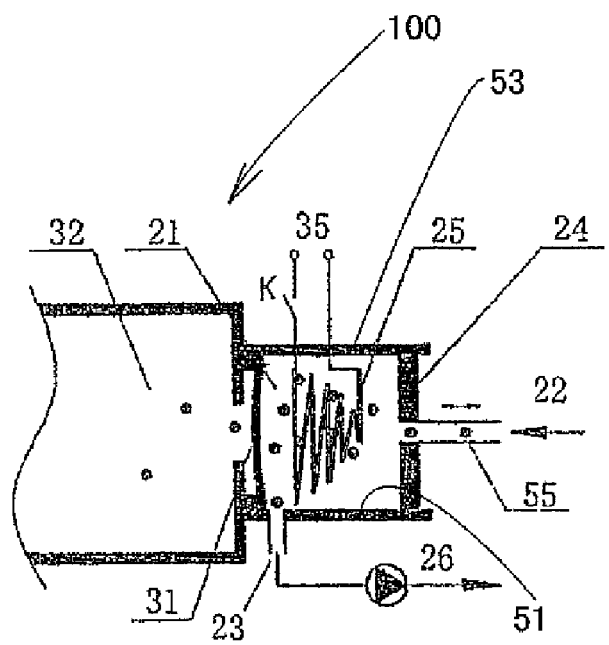
FIG. 1 is a schematic diagram showing a process of feeding sample by gas prior to gas pre-concentrating process according to the present invention.

A trace detector and an analytical method for a trace detector according to the present invention will be described with reference to FIGS. 1-2.

Firstly, a trace detector 100 according to the present invention will be described with reference to FIGS. 1-2. Referring to FIGS. 1-2, the trace detector 100 comprises a desorption chamber 51 defining a desorption region 21 and a controller (not shown). The desorption chamber 51 has a housing 53. The housing 53 has a sample feeding port 22 for introducing a substance 55 to be detected into the desorption chamber 51 and a gas discharge port 23 for discharging gas entraining the sample from the desorption chamber 51. The controller is used for controlling the trace detector 100 in such a manner that the sample feeding port 22 and the gas discharge port 23 are in fluid communication with the desorption chamber during pre-concentration process of the trace detector 100, thereby continuously feeding and collecting the sample.

The trace detector may be instruments such as an ion mobility spectrometer, for detecting explosives, narcotics and the like. As shown in FIGS. 1-2, the gas discharge port 23 is connected to a sample feeding pump 26 through a pipe, and a semi-permeable membrane 31 is disposed between the desorption region 21 and an ionization region 32.

The housing further comprises a movable portion. The volume of the desorption chamber 51 can be changed by moving the movable portion to achieve the gas pre-concentration process. For example, a part of the housing may be flexible and thus the volume of the desorption chamber can be changed through the flexible part of the housing. Apparently, the movable portion may be any device that can change the volume of the desorption chamber.

Figure 2:
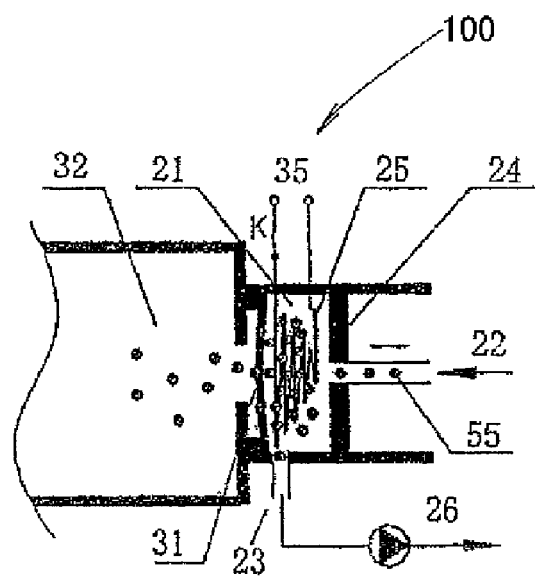
FIG. 2 is a schematic diagram showing a state in which gas pre-concentrating process is performed while the sample feeding process is being carried out according to the present invention.

In the embodiment shown in FIGS. 1-2, the housing further comprises a side wall forming a cylindrical internal space. The movable portion is a movable member 24. The movable member 24 is slidably disposed in the internal space to change the volume of the internal space. The internal space may have a cylindrical shape, a prismatic shape or any appropriate column shape. The movable member 24 has a shape corresponding to a shape of a cross-section of the internal space to move in the internal space as a piston while the movable member 24 is in tight contact with the side wall.

The trace detector may further comprise a trapping carrier 25 as a desorber. The trapping carrier is disposed in the desorption chamber and has a strong absorbability for a substance to be detected and a large specific surface area. The trapping carrier functions as a desorber during the gas pre-concentrating process. The desorber may be made of a material having a large specific surface area and a strong absorbability. The trapping carrier 25 is coupled with a power source 35 through a switch K for heating.

In order to improve desorption efficiency, the controller may control a temperature of the desorption region and/or a flow rate of the gas entraining sample and discharged from the gas discharge port of the desorption chamber during the gas pre-concentration process and the desorption process of the trace detector. Alternatively, in order to improve desorption efficiency, the controller may control a flow rate of the sample gas or the gas entraining the sample.

Preferably, improvement of the temperature of the desorption region is a process in which the temperature of the desorption rises quickly while the sample is desorbed and released quickly.

With the above operation manner, the desorption efficiency is increased during the gas pre-concentration process, thereby improving detection efficiency of the detector during the gas pre-concentration process.

Next, an analytical method for a trace detector according to the present invention will be described with reference to FIGS. 1-2. The analytical method for a trace detector comprises the steps of: continuously feeding sample into a desorption chamber of the trace detector; continuously discharging gas entraining the sample from the desorption chamber; and pre-concentrating the gas entraining the sample or the sample gas in the desorption chamber while continuously feeding the sample into the desorption chamber and continuously discharging the gas entraining the sample. By simultaneously performing the pre-concentrating step, the feeding step and the discharging step, the trace detector has an excellent detecting period of time whether the substance to be detected in the sample gas is in a high concentration state or a low concentration state, and the trace detector can perform continuous sampling for a long time.

The analytical method for a trace detector according to the present invention may further comprise the step of continuously collecting, processing and analyzing the sample. In other words, the sample is continuously collected, processed and analyzed while continuously feeding sample into the desorption chamber and continuously discharging the gas entraining the sample.

The analytical method for a trace detector may further comprise the step of changing a volume of the desorption chamber to achieve the gas pre-concentration process.

According to an embodiment of the present invention, the analytical method for a trace detector may further comprise the step of controlling or changing a temperature of the desorption region and/or a flow rate of the gas entraining the sample and discharged from the desorption chamber.

Preferably, improving the temperature of the desorption region comprises increasing the temperature of the desorption region quickly.

What is claimed is:

1. A trace detector, comprising:
a desorption chamber defining a desorption region, the desorption chamber having a housing, the chamber having a sample feeding port for introducing a sample to be detected into the desorption chamber and a gas discharge port for discharging gas entraining the sample from the desorption chamber; wherein the sample feeding port and the gas discharge port are in fluid communication with the desorption chamber during pre-concentrating gas entraining the sample in the desorption chamber of the trace detector by changing a volume of the desorption chamber, thereby continuously feeding and collecting the sample.

2. The trace detector according to claim 1, wherein the chamber further has a movable portion, and the volume of the desorption chamber can be changed by moving the movable portion.

3. The trace detector according to claim 2, wherein the chamber has a side wall forming a substantially cylindrical internal space, and the movable portion comprises a movable member, the movable member being slidably disposed in the internal space to change the volume of the internal space.

4. The trace detector according to claim 3, wherein a temperature of the desorption region and/or a flow rate of the gas which entrains the introduced sample and is discharged from the gas discharge port of the desorption chamber is changed during sampling and analyzing of the trace detector.

5. The trace detector according to claim 4, wherein improvement of the temperature of the desorption region is a process in which the temperature of the desorption rises quickly.

6. The trace detector according to claim 5, wherein the trace detector is an ion mobility spectrometer.

7. An analytical method for a trace detector, comprising the steps of:
continuously feeding a sample into a desorption chamber of the trace detector, the desorption chamber defining a desorption region;
continuously discharging gas entraining the sample from the desorption chamber; and
pre-concentrating the gas entraining the sample in the desorption chamber by changing a volume of the desorption chamber while continuously feeding the sample into the desorption chamber and continuously discharging the gas entraining the sample.

8. The analytical method according to claim 7, further comprising the step of:
continuously collecting, processing and analyzing the sample.

9. The analytical method according to claim 7, further comprising the step of:
controlling or changing a temperature of the desorption region and/or a flow rate of the gas which entrains the fed sample and is discharged from the desorption chamber.

10. The analytical method according to claim 9, wherein the step of controlling the temperature of the desorption region comprises increasing the temperature of the desorption region quickly.

* * * * *